US012577333B2

(12) United States Patent
Ballard et al.

(10) Patent No.: US 12,577,333 B2
(45) Date of Patent: ***Mar. 17, 2026

(54) CROSSLINKED PTFE

(71) Applicant: ZEUS COMPANY LLC, Orangeburg, SC (US)

(72) Inventors: Robert L. Ballard, Lexington, SC (US); John Richard Campanelli, West Columbia, SC (US); Patrick Cooper, Orangeburg, SC (US); Justin A. Marro, Orangeburg, SC (US); Douglas Lee Tourville, Orangeburg, SC (US); Bhavya Singhi, Orangeburg, SC (US)

(73) Assignee: ZEUS COMPANY LLC, Orangeburg, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/643,172

(22) Filed: Apr. 23, 2024

(65) Prior Publication Data

US 2024/0287221 A1 Aug. 29, 2024

Related U.S. Application Data

(63) Continuation of application No. 17/834,315, filed on Jun. 7, 2022, now Pat. No. 11,993,666, which is a continuation of application No. PCT/US2020/065204, filed on Dec. 16, 2020.

(60) Provisional application No. 62/948,369, filed on Dec. 16, 2019.

(51) Int. Cl.
| | |
|---|---|
| *A61L 29/04* | (2006.01) |
| *A61L 29/14* | (2006.01) |
| *B29C 48/00* | (2019.01) |
| *B29C 48/10* | (2019.01) |
| *B29C 71/04* | (2006.01) |
| *B29K 27/18* | (2006.01) |
| *B29L 31/00* | (2006.01) |
| *C08F 114/26* | (2006.01) |

(52) U.S. Cl.
CPC .......... *C08F 114/26* (2013.01); *A61L 29/041* (2013.01); *B29C 48/022* (2019.02); *B29C 48/10* (2019.02); *B29C 71/04* (2013.01); *A61L 29/14* (2013.01); *B29C 2791/005* (2013.01); *B29K 2027/18* (2013.01); *B29L 2031/7542* (2013.01)

(58) Field of Classification Search
None
See application file for complete search history.

(56) References Cited

U.S. PATENT DOCUMENTS

| | | | | |
|---|---|---|---|---|
| 11,993,666 B2 * | 5/2024 | Ballard | .................. | B29C 71/04 |
| 2007/0282031 A1 * | 12/2007 | Lehmann | .............. | C08F 259/08 |
| | | | | 522/3 |

FOREIGN PATENT DOCUMENTS

| | | | |
|---|---|---|---|
| JP | 2006158766 | * | 8/2011 |

* cited by examiner

*Primary Examiner* — Yan Lan
(74) *Attorney, Agent, or Firm* — WOMBLE BOND DICKINSON (US) LLP; Jessica L. Gorczynski

(57) ABSTRACT

The present application relates generally to tubes, such as thin walled catheter liners with small wall thicknesses (e.g., less than 1 mm), including crosslinked fluoropolymers, e.g., crosslinked poly(tetrafluoroethylene). The disclosure further provides methods of manufacturing such tubes and systems for manufacturing such tubes.

18 Claims, 2 Drawing Sheets

CROSSLINKED PTFE

CROSS-REFERENCE TO RELATED APPLICATIONS

The present application is a continuation of U.S. patent application Ser. No. 17/834,315, filed Jun. 7, 2022; which application is a continuation of PCT Application no. PCT/US2020/065204, filed Dec. 16, 2020; which application claims the benefit of U.S. Provisional Application No. 62/948,369, filed Dec. 16, 2019. The disclosures of the aforementioned applications are incorporated herein by reference in their entirety.

FIELD OF THE INVENTION

The present application is directed to crosslinked fluoropolymeric products and methods for making such crosslinked products, which find application in a variety of fields.

BACKGROUND

Polytetrafluoroethylene (PTFE) has low coefficient of friction, along with excellent chemical resistance and thermal stability. This makes it an ideal polymer for various industrial and medical applications. For medical devices such as catheters with PTFE liners, the currently preferred sterilization method is the use of ethylene oxide (ETO). Recently, there has been an increased desire on the part of device manufacturers to employ radiation-based sterilization using electron beam or gamma sources. Irradiation is one of the most widely used sterilization processes for medical devices. It streamlines the sterilization process since it can be quickly performed in line, while the ETO gas sterilization procedure requires storage for up to 48 hours to allow the gas to diffuse out of the sterilized device post-exposure. Unfortunately, PTFE polymer chains are highly susceptible to chain scission when irradiated, thereby leading to an unacceptable loss in physical properties.

U.S. Pat. No. 5,444,103 to Tabata et al. describes a batch process for modifying PTFE sheets and improving their radiation resistance by subjecting them to radiation at high temperatures in an inert atmosphere. Such treatment was noted to crosslink the polymer chains and alter the mechanical properties of the sheet-based product, leading to increased strength, lower elongation or higher toughness. However, batch processes tend to be cumbersome, expensive and not well-suited to modern PTFE liner extrusion processes. It would be advantageous to provide further methods to give polymeric products with improved radiation resistance.

SUMMARY

The present disclosure is directed to a continuous method to crosslink poly(tetrafluoroethylene) ("PTFE") and other fluoropolymers by irradiation at high temperatures as well as tubes and profiles made from such a method. Crosslinked PTFE is more resistant to gamma and electron-beam irradiation, which is known to degrade the physical properties of PTFE by inducing scission of the polymer chains. Radiation resistance is desirable in applications where PTFE-containing articles, such as medical devices, are sterilized through irradiation by gamma sources or electron beams.

In one embodiment is provided a method for continuously extruding, sintering and irradiating PTFE to produce crosslinked PTFE tube or profile. The disclosure provides for increased efficiency obtained by taking the tube or profile directly from the extrusion/sintering process into a crosslinking chamber so that the temperature of the tube or profile is sufficient (e.g., optimal or near-optimal) to promote crosslinking of the PTFE under gamma, electron beam or X-ray irradiation. A further aspect of the increased efficiency is provided by the continuous nature of the crosslinking process, which is well suited to large scale production of the inventive crosslinked tubes or profiles.

The disclosed method further allows for the addition of a range of reactive chemical species, e.g., in a controlled fashion, to the inert gas during irradiation in the crosslinking operation. Such a process can allow for the creation of a functionalized PTFE surface (modified with the reactive chemical species added) in the extruded part or profile.

The chamber, equipment and operating parameters associated with the crosslinking operation must be optimized for the extrusion of thin-walled tubes so that the ability of the polymer chains to crosslink under irradiation is not impeded by the molecular orientation imparted during the extrusion operation or by morphological changes associated with the sintering operation. Moreover, the crosslinking operation must be carried out in such a manner as to optimize extrusion line speed and radiation exposure in order to ensure that sufficient energy dosage is absorbed by the tube or profile thereby enabling optimal crosslinking of the polymer.

The continuous crosslinking process method can be applied to the manufacturing of other PTFE products, such as electrospun mats, dip coated tubes and extruded monofilaments. It can also be applied to other fluoropolymers such as FEP (fluorinated ethylene propylene) or PFA (perfluoroalkoxy alkanes) and their associated manufacturing methods in addition to extrusion, including blow molding, compression molding, and injection molding.

The continuous crosslinking process of the invention has benefits of low cost, speed and efficiency that are amenable to industrial-scale manufacturing of tubes and profiles.

In the desired end use applications, crosslinking of PTFE liners and profiles as described herein will allow gamma, e-beam and X-ray sterilization of medical devices containing said liners without undue degradation of their physical properties. Moreover, a PTFE liner with a functionalized surface created during the crosslinking operation may, in some embodiments, not require subsequent etching, thereby eliminating a costly operation and further streamlining the manufacturing process of tubes for catheter applications.

The disclosure includes, without limitations, the following embodiments.

Embodiment 1: A tube having a wall thickness of less than 1 mm, comprising crosslinked poly(tetrafluoroethylene).

Embodiment 2: The tube of Embodiment 1, wherein the tube consists essentially of crosslinked poly(tetrafluoroethylene).

Embodiment 3: The tube of any of Embodiments 1-2, wherein the poly(tetrafluoroethylene) has been crosslinked in a continuous process by irradiation with a gamma source under the following conditions: a. a temperature range between 320-360° C.; b. a dosage between 500 and 2500 kGy; and c. an inert atmosphere or vacuum.

Embodiment 4: The tube of any of Embodiments 1-3, wherein the irradiation is provided by an X-ray source.

Embodiment 5: The tube of any of Embodiments 1-4, wherein the irradiation is provided by an electron beam unit.

Embodiment 6: The tube of any of Embodiments 1-5, wherein at least a part of an inner or outer surface of the tube comprises the crosslinked poly(tetrafluoroethylene) chemically modified with at least one reactive species.

Embodiment 7: The tube of any of Embodiments 1-6, wherein only the inner surface of the tube comprises the crosslinked poly(tetrafluoroethylene) chemically modified with at least one reactive species.

Embodiment 8: The tube of any of Embodiments 1-6, wherein only the outer surface of the tube comprises the crosslinked poly(tetrafluoroethylene) chemically modified with at least one reactive species.

Embodiment 9: A tube having a wall thickness of less than 1 mm, comprising a crosslinked fluoropolymer, wherein the fluoropolymer has been crosslinked in a continuous process by irradiation with a gamma source under the following conditions: a. a temperature range corresponding to a range of a melting endotherm of the fluoropolymer in a differential scanning calorimeter (DSC) scan; b. a dosage between 500 and 2500 kGy; and c. an inert atmosphere or vacuum.

Embodiment 10: The tube of Embodiment 9, wherein irradiation is provided by an X-ray source.

Embodiment 11: The tube of any of Embodiments 9-10, wherein irradiation is provided by an electron beam unit.

Embodiment 12: The tube of any of Embodiments 9-11, wherein at least a part of an inner or outer surface of the tube comprises the crosslinked poly(tetrafluoroethylene) chemically modified with at least one reactive species.

Embodiment 13: The tube of any of Embodiments 9-12, wherein only the inner surface of the tube comprises the crosslinked poly(tetrafluoroethylene) chemically modified with at least one reactive species.

Embodiment 14: The tube of any of Embodiments 9-12, wherein only the outer surface of the tube comprises the crosslinked poly(tetrafluoroethylene) chemically modified with at least one reactive species.

Embodiment 15: A method of providing a crosslinked fluoropolymeric product, comprising: providing a fluoropolymer-containing intermediate; irradiating the fluoropolymer-containing intermediate with a gamma source under the following conditions: a. a temperature range corresponding to a range of a melting endotherm of the fluoropolymer in a differential scanning calorimeter (DSC) scan; b. a dosage between 500 and 2500 kGy; and an inert atmosphere or vacuum.

Embodiment 16: The method of Embodiment 15, wherein the fluoropolymer-containing intermediate comprises poly(tetrafluoroethylene), and wherein the irradiating comprises irradiating the fluoropolymer-containing intermediate with the gamma source under the following conditions: a. a temperature range between 320-360° C.; b. a dosage between 500 and 2500 kGy; and c. an inert atmosphere or vacuum.

Embodiment 17: The method of any of Embodiments 15-16, wherein irradiation is provided by an X-ray source.

Embodiment 18: The method of any of Embodiments 15-17, wherein irradiation is provided by an electron beam unit.

Embodiment 19: The method of any of Embodiments 15-18, wherein the fluoropolymer-containing intermediate comprises a tube, profile, or electrospun mat.

Embodiment 20: The method of any of Embodiments 15-19, wherein the irradiating is done immediately following a step of sintering the poly(tetrafluoroethylene), such that the fluoropolymer-containing intermediate is at an elevated temperature from the sintering step immediately upon beginning the irradiating step.

Embodiment 21: The method of Embodiment 20, wherein the sintering and irradiating are in-line steps.

Embodiment 22: The method of any of Embodiments 15-21, employed for the production of the tube of any of Embodiments 1-14.

Embodiment 23: A system for the production of crosslinked polymeric products comprising poly(tetrafluoroethylene), comprising a sintering unit and an in-line crosslinking chamber.

These and other features, aspects, and advantages of the disclosure will be apparent from a reading of the following detailed description together with the accompanying drawings, which are briefly described below. The invention includes any combination of two, three, four, or more of the above-noted embodiments as well as combinations of any two, three, four, or more features or elements set forth in this disclosure, regardless of whether such features or elements are expressly combined in a specific embodiment description herein. This disclosure is intended to be read holistically such that any separable features or elements of the disclosed invention, in any of its various aspects and embodiments, should be viewed as intended to be combinable unless the context clearly dictates otherwise.

BRIEF DESCRIPTION OF THE DRAWINGS

In order to provide an understanding of embodiments of the invention, reference is made to the appended drawings, which are not necessarily drawn to scale, and in which reference numerals refer to components of exemplary embodiments of the invention. The drawings are exemplary only, and should not be construed as limiting the invention.

DETAILED DESCRIPTION

The present invention will now be described more fully hereinafter with reference to the accompanying figures, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Figure 1:
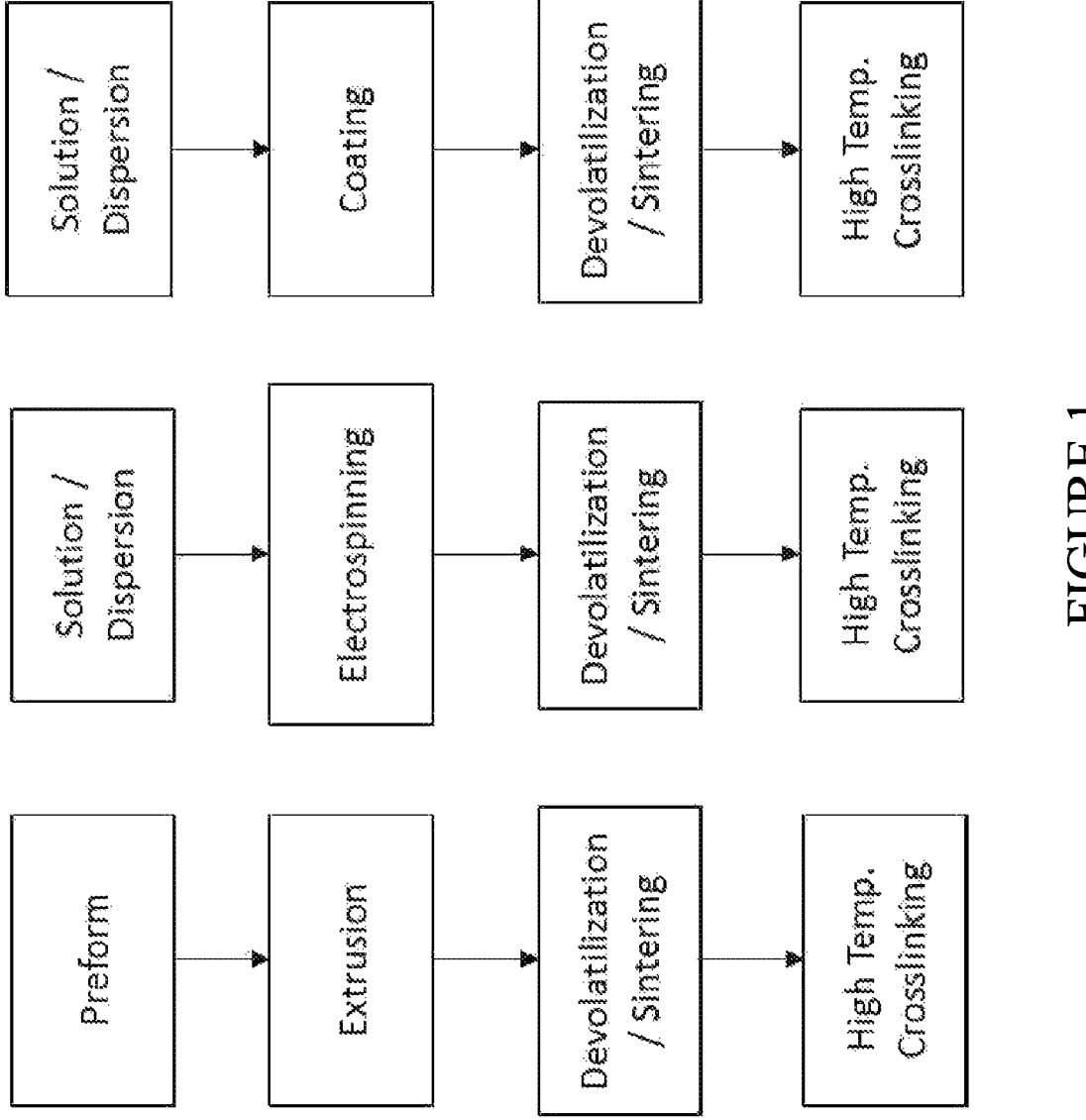
FIG. 1 is a schematic representation of various in-line continuous processes for the cross-linking of PTFE-containing intermediates according to certain embodiments of the disclosure.

The disclosure provides a process for the production of crosslinked, radiation-stable fluoropolymeric products, and also provides such fluoropolymeric products. At least a portion of the process can advantageously be continuous, i.e., the disclosed steps can be done in immediate succession (without significant interruption). The steps of the process generally include: forming a PTFE-containing intermediate, devolatilization/sintering of the intermediate to give a sintered intermediate, and cross-linking the sintered intermediate to provide the crosslinked PTFE-containing product. In some embodiments, at least the devolatilization/sintering and cross-linking steps are conducted in a continuous manner. Certain embodiments of processes falling within the scope of this disclosure are illustrated in FIG. 1.

The forming step can vary. FIG. 1 shows several, non-limiting processes for "forming" a PTFE-containing intermediate, namely, providing a preform and extrusion; providing a solution or dispersion and electrospinning the solution or dispersion; and providing a solution or dispersion and coating the solution or dispersion onto a substrate. It is to be noted that these forming steps provided herein are not intended to be limiting; any process suitable for providing a PTFE-containing intermediate (e.g., a tube, a sheet, a mat, a profile, a monofilament, and the like) that is advantageously subsequently crosslinked can be used in this step.

In some embodiments, the forming step may comprise preparing a preform and extruding. For example, in one embodiment, poly(tetrafluoroethylene) ("PTFE") powder can be combined or compounded with a lubricant, solvent or mixture to make a preform. One exemplary method involves preparing a preform comprising PTFE fine powder and a chemical lubricant such as naphtha to give a material in paste form. The resulting preform is generally in a paste-like or otherwise moldable form that is passed through an annular die to form an extruded PTFE-containing intermediate (e.g., a tube). Methods of making preforms of PTFE and various other polymers and extruding such preforms, which can be used as a first (forming) step of the disclosed process are generally known in the art, e.g., as disclosed in U.S. Pat. No. 10,744,231 to Wahab et al., which is incorporated herein by reference in its entirety.

In other embodiments, the forming step may comprise electrospinning. Electrospinning methods are generally known, and PTFE dispersions in water or other solvents or solvent blends can be used. One method for electrospinning PTFE is described, for example, in U.S. Pat. No. 8,178,030 to Anneaux et al., which is incorporated herein by reference in its entirety. An electrospun web or mat can be produced via such processes and, in some embodiments, such a PTFE-containing intermediate is provided in the form of such a web or mat on a suitable substrate.

In still other embodiments, the forming step may comprise providing a coating of PTFE on another material. For example, a PTFE solution or dispersion can be used in a dip coating operation to coat a substrate (e.g., a mandrel or tube) to give the PTFE-containing intermediate. Dip coating generally involves immersing a substrate in a solution or dispersion of the desired coating material (e.g., PTFE). Other coating methods, e.g., spray coating (including conventional and air atomized spraying and electrostatic coating), can also be employed to provide a coated PTFE-containing intermediate.

The PTFE-containing intermediate (prepared via a forming step, including, but not limited to those outlined above) is then subjected to a devolatilization/sintering step. In this step, the PTFE-containing intermediate is subjected to devolatilization operations where residual lubricants, solvents or water are removed. This operation is followed by sintering at temperatures near or exceeding the melting point of PTFE (i.e., close to or greater than 327° C.) in order to fuse individual PTFE particles together. During the devolatilization/sintering process, the temperature of the intermediate product (e.g., tube or profile) can, in some embodiments, reach or exceed the region in which the crosslinking of PTFE is subsequently achieved.

The sintered PTFE-containing intermediate is then subjected to the crosslinking step. This step is advantageously positioned immediately following the devolatilization and sintering operations to take advantage of the temperature of the sintered intermediate at that stage (which would typically be close to the melt temperature of PTFE). As such, these steps can, in some embodiments, comprise a continuous, e.g., in-line process where the heated, sintered intermediate is directly subjected to the crosslinking step to take advantage of the elevated temperature of the sintered intermediate.

Figure 2:
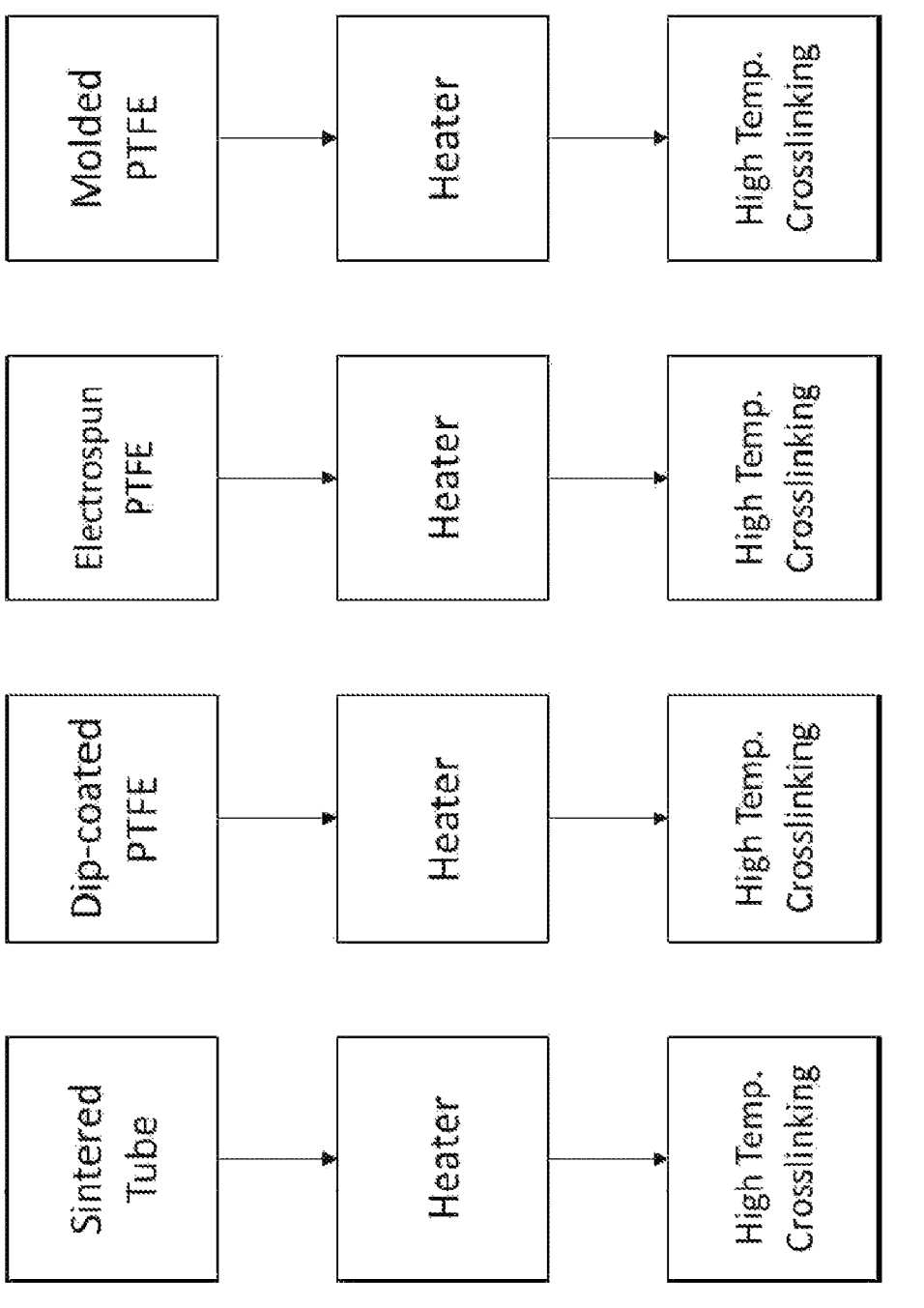
FIG. 2 is a schematic representation of various continuous processes for the cross-linking of PTFE-containing intermediates employing heating as a secondary operation according to certain embodiments of the disclosure.

However, it is noted that, in some embodiments, this immediate/in-line connection between the devolatilization/sintering step and the subsequent crosslinking step is not desirable or feasible. Thus, in some embodiments, one or more secondary operations may be introduced within the disclosed process. In some such embodiments, a heated sintered intermediate may not be reasonably maintained at an elevated temperature following the devolatilization/sintering. In such embodiments, a heater may be employed between the devolatilization/sintering step and the crosslinking step, e.g., as shown in FIG. 2. In some such embodiments, the sintered intermediate (e.g., a sintered PTFE-containing tube, a sintered PTFE-containing profile, a PTFE-containing dip-coated or solution-coated substrate, e.g., tube, or a PTFE-containing molded sheet/plaque/part) is heated up to the target temperature (e.g., the temperature at which crosslinking will be conducted) in an inert atmosphere or vacuum and subsequently irradiated in a crosslinking chamber as described herein.

The crosslinking step is typically conducted within a crosslinking chamber, containing a vacuum or an inert gas such as argon or nitrogen. Any chamber suitable to accommodate the PTFE-containing intermediate within a controlled environment can be used. As such, the sintered PTFE-containing intermediate must typically be moved after the devolatilization/sintering step into a suitable crosslinking chamber. The radiation energy supplied to the sintered intermediate in the crosslinking chamber can be provided from various sources, and is preferably from an X-ray source, a gamma source, or an electron beam unit. Electron beam units useful for industrial purposes are sold, for example, by Wasik Associates Inc. (Dracut, MA). It is important that the PTFE intermediate absorbs a sufficient dosage of energy for crosslinking to occur within the crosslinking chamber. The absorption of energy by the intermediate can be optimized by controlling the energy output of the radiation source or by controlling the residence time of the PTFE intermediate within the crosslinking chamber or by controlling both. Residence time within the crosslinking chamber can be controlled in various ways known to those skilled in the art including the manipulation of line speeds and the use of mechanical inventories within the chamber. Some important processing parameters for the crosslinking operation are summarized in Table 1.

TABLE 1

Some Operating Parameters for the Crosslinking Operation

| Crosslinking Chamber Parameter | Details |
| --- | --- |
| Irradiation source | Gamma, electron beam, X-ray |
| Dosage level absorbed, kGy | 500-2500 |
| Temperature of PTFE, ° C. | 320-360 |
| Atmosphere | Inert gas or vacuum |

If, for example, a 300 keV electron beam unit is used in the crosslinking step, the current required to deliver the desired dosage could be calculated using Equation 1 below.

$$\text{Dose } [kGy] = k' \left[ kGy \cdot \text{m/mA} \cdot \text{min} \right] \cdot I[\text{mA}]/S[\text{m/min}] \qquad \text{Equation 1}$$

where k' is the production constant, I is the beam current, and S is the line speed.

In some embodiments, the crosslinking step takes place solely in the presence of the referenced inert gas or vacuum environment within the crosslinking chamber. In other embodiments, one or more reactive species can be introduced with the inert gas into the crosslinking chamber in order to functionalize the PTFE surfaces. Functionalizing a surface is understood to mean chemically modifying the PTFE surface of the intermediate within the chamber so that moieties of the reactive species are chemically bonded to the polymer chains at or near the surface of the intermediate (e.g., tube, mat or profile). Non-limiting examples of reactive species that could be used for functionalization of PTFE surfaces include oxygen, acrylic acid, maleic anhydride, epoxides, isocyanates, silanes, and others well-known to those skilled in the art.

In one particular embodiment, such a process can be applied to a PTFE-containing intermediate in the form of a tube, where reactive species can be introduced in such a manner that they are localized on the inside or outside surface of the tube (maintaining an inert atmosphere on the other of the inside or outside of the tube), or reactive species can be present on both the inside and outside of the tube. Similarly, such a process can be applied to one side of a PTFE-containing intermediate in other forms (e.g., in the form of a mat or profile), by maintaining an inert atmosphere on one surface to promote crosslinking, while introducing reactive species on the other surface of the intermediate to functionalize that surface independently. In some embodiments, two surfaces can be functionalized with different reactive species via such methods.

This ability to independently functionalize (or not functionalize) different sides of such PTFE-containing intermediates during the crosslinking step could be useful, for example, in making the outer surface of a PTFE tube hydrophilic for enhanced bondability in catheter manufacturing. Functionalizing the outer surface of a PTFE tube in such embodiments as described herein could eliminate the need for a subsequent etching operation and thereby lower production costs. e.g., by eliminating used etchant as a hazardous waste stream. In some embodiments, functionalizing the inner surface of a PTFE-containing tube to render it hydrophilic would result in an increased lubricity of the lumen in aqueous or saline solutions.

Following the crosslinking step, the PTFE product is removed from the chamber. In some embodiments, this product is complete, i.e., no further processing is required. In some embodiments, one or more further (downstream) operations can be conducted on the PTFE product. Various operations can be incorporated into the process as desired depending on the requirements of the final product. Such further operations include, but are not limited to, etching to activate the PTFE surface, winding, coiling, cutting and/or printing. Additional secondary processing operations such as laminating, stretching and expanding can be performed on the crosslinked PTFE as generally known to persons skilled in the art.

The disclosure further provides a system suitable to provide a product using the method outlined herein. In particular, the system in some embodiments comprises a unit for devolatilization/sintering and an inline chamber for crosslinking. Other components can be provided within the disclosed system in various embodiments (e.g., upstream equipment suitable for conducting the forming step, such as an electrospinning apparatus, a coating apparatus, and/or an extruder). In one particular embodiment, an extruder, unit for devolatilization/sintering, and chamber for crosslinking are all in line with one another. Further components can provide for downstream processing, as referenced above. Such other components may be in line with the unit for devolatilization/sintering and/or the chamber for crosslinking or may be provided separately. The rate/line speed can vary without deviating from the scope of this disclosure and may be modified. e.g., based on the total dosage rate to be applied within the chamber and the dosage provided by the irradiation source.

It is to be understood by a person skilled in the art that the disclosed process is not limited to the production of only PTFE-containing products (and, correspondingly, the disclosed products and system are not relevant only to PTFE-containing materials). In some embodiments, the disclosed process is applicable to the production of products that consist or consist essentially of PTFE, as well as to products that contain one or more additional components in addition to PTFE. As such. PTFE may comprise a majority or a minority of the product by weight. In other embodiments, the process is applicable to the production of other types of crosslinked products, e.g., products comprising other crosslinked fluoropolymers. In some such non-limiting embodiments, the process is applicable for products comprising EFEP (a terpolymer of ethylene, tetrafluoroethylene, and hexafluoropropylene), FEP (fluorinated ethylene propylene), ETFE (ethylene tetrafluoroethylene), PFA (perfluoroalkoxy alkanes), and copolymers and derivatives thereof. One of skill in the art will appreciate that certain parameters of the process outlined herein would require modification, depending upon the particular polymer or polymer to which the method is applied. In some embodiments, an appropriate temperature within the crosslinking chamber can be determined by evaluating the differential scanning calorimeter (DSC) scan of the material comprising the intermediate. A suitable temperature range to which the intermediate is subjected within the crosslinking chamber, in some embodiments, corresponds to a range of a melting endotherm of the fluoropolymer in the DSC scan.

The process provided herein has various applications, and can be used for preparing a range of different types of products. Examples of the types of products that can be produced and crosslinked via the disclosed process include, but are not limited to: tubes such as catheter liners (including extruded liners) and, in particular thin-walled catheter liners, dipped liners, shrinkable tubes, extruded or dipped liners over wire or mandrel; monofilaments, including expanded monofilaments; extruded profiles of various sizes and shapes; ribbons; membranes, including electrospun membranes, webs, or mats.

The products prepared by the disclosed method can, in some embodiments, have advantageous physical properties. Furthermore, products provided according to the disclosed methods (including tubes and other shapes/products as described herein) are advantageously endowed with gamma, and e-beam resistance (particularly relevant in the context of medical devices). Such products can, in some embodiments, exhibit increased stability of physical properties, which is an important feature (e.g., wherein the product is to be used in procedures using X-rays to guide a catheter). In further embodiments, products produced according to the disclosed process can exhibit, in some embodiments, features including high optical clarity, low elongation at break, enhanced toughness, and/or increased strength.

In certain embodiments, crosslinked PTFE-containing tubes, e.g., crosslinked extruded PTFE tubes (which comprise, consist essentially of, or consist of PTFE) are uniquely provided according to the present disclosure. In some embodiments, crosslinked PTFE-containing tubes provided via the disclosed method can exhibit certain characteristic physical properties that render them improved in one or more aspects as compared with current extruded tubes (e.g., those that have not been subjected to the crosslinking step after production). Such tubes may have, for example, one or more of the following physical properties in comparison to current extruded tubes: lower elongation at break; higher modulus and tensile strength; higher optical clarity; lower crystallinity; enhanced toughness; and increased strength. Methods of evaluating such properties are known in the art and could be readily determined by one of ordinary skill in the art.

Aspects of the present disclosure are more fully illustrated by the following examples, which are set forth to illustrate certain aspects of the disclosure and are not meant to be construed as limiting thereof.

Example 1

A PTFE tube with an outer diameter (OD) of 0.07" and a wall thickness of 0.002" is extruded from a preform using naphtha as the lubricant in a paste extruder. Upon exiting the sintering operation and entering the crosslinking chamber, the PTFE tube is at a temperature close to 340° C. The tube temperature is maintained in the crosslinking chamber within ±10° C. of the entry temperature. The crosslinking chamber is fed with dry argon gas to provide a positive pressure within the chamber so no air or humidity can enter with the tube. The inner diameter of the tube is flushed with argon through the mandrel of the extruder and into the lumen of the tube. The tube is irradiated with a 300 keV e-beam unit equipped with filament arrays to expose the tube OD surface evenly to the beam so that an overall energy dosage of 500 kGy is absorbed according to Equation 1. Upon exiting the chamber, the tube passes through an etch solution, is dried and is cut into 48" lengths. The cut crosslinked tubes are found to have a higher clarity and tensile strength compared to uncrosslinked traditional tubes.

Example 2

In a process analogous to that described in Example 1 above, 1% acrylic acid (v/v) is introduced into the crosslinking chamber with the argon gas. All other process parameters are maintained the same as in Example 1. After the tube exits the chamber, it is not passed through an etching solution. The tube OD is found to have a contact angle against water of less than 90°.

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

We claim:

1. A tube having a wall thickness of less than 1 mm, wherein the tube consists essentially of crosslinked poly (tetrafluoroethylene), chemically modified with at least one reactive species; and wherein the crosslinked poly(tetrafluoroethylene) has been crosslinked in an inert atmosphere containing a reactive species.

2. The tube of claim 1, wherein the at least one reactive species activates one or more walls or surfaces of the tube to provide reactive sites on those surfaces.

3. The tube of claim 1, wherein the crosslinking is conducted at a temperature range between 320-360° C.

4. The tube of claim 1, wherein the crosslinking is conducted by irradiation.

5. The tube of claim 4, wherein the irradiation is provided by an X-ray source.

6. The tube of claim 4, wherein the irradiation is provided by an electron beam unit.

7. The tube of claim 1, wherein only the inner surface of the tube comprises the crosslinked poly(tetrafluoroethylene) chemically modified with at least one reactive species.

8. The tube of claim 1, wherein only the outer surface of the tube comprises the crosslinked poly(tetrafluoroethylene) chemically modified with at least one reactive species.

9. The tube of claim 4, wherein the irradiation is at a dose of between 500 and 2500 kGy.

10. The tube of claim 1, wherein the inner and outer surfaces of the tube comprise the crosslinked poly(tetrafluoroethylene) chemically modified with at least one reactive species.

11. The tube of claim 10, wherein the inner and outer surfaces comprise the same reactive species.

12. The tube of claim 10, wherein the inner and outer surfaces comprise different reactive species.

13. The tube of claim 1, wherein the inner surface of the tube comprises the crosslinked poly(tetrafluoroethylene) chemically modified with at least one reactive species, and wherein the at least one reactive species has increased hydrophilicity relative to crosslinked poly(tetrafluoethylene).

14. The tube of claim 1, wherein the outer surface of the tube comprises the crosslinked poly(tetrafluoroethylene) chemically modified with at least one reactive species, and wherein the at least one reactive species has increased hydrophilicity relative to crosslinked poly(tetrafluoethylene).

15. The tube of claim 1, wherein the at least one reactive species is selected from the group consisting of oxygen, acrylic acid, maleic anhydride, an epoxide, an isocyanate, a silane, or any combination thereof.

16. A catheter comprising the tube of claim 1 as a liner.

17. A catheter comprising the tube of claim 13 as a liner.

18. A catheter comprising the tube of claim 14 as a liner.

* * * * *